(12) United States Patent
Nishikubo et al.

(10) Patent No.: US 7,057,063 B2
(45) Date of Patent: Jun. 6, 2006

(54) UNSATURATED CARBOXYLIC ESTER COMPOUND, PROCESS FOR PRODUCING THE SAME, AND COMPOSITION CURABLE WITH ACTINIC ENERGY RAY

(75) Inventors: Tadatomi Nishikubo, Fujisawa (JP); Atsushi Kameyama, Yokohama (JP); Masaki Sasaki, Asaka (JP); Masatoshi Kusama, Sakado (JP)

(73) Assignees: Kanagawa University (JP); Taiyo Ink Manufacturing Co., Ltd. (JP)

( * ) Notice: Subject to any disclaimer, the term of this patent is extended or adjusted under 35 U.S.C. 154(b) by 316 days.

(21) Appl. No.: 10/202,092

(22) Filed: Jul. 25, 2002

(65) Prior Publication Data

US 2003/0009053 A1    Jan. 9, 2003

Related U.S. Application Data

(63) Continuation of application No. PCT/JP01/00447, filed on Jan. 24, 2001, now abandoned.

(30) Foreign Application Priority Data

Jan. 27, 2000 (JP) .............................. 2000-018327
Mar. 29, 2000 (JP) .............................. 2000-090887

(51) Int. Cl.
*C07C 69/76* (2006.01)
(52) U.S. Cl. ....................................................... 560/90
(58) Field of Classification Search ................ 560/205, 560/220, 221
See application file for complete search history.

(56) References Cited

FOREIGN PATENT DOCUMENTS

| | | | |
|---|---|---|---|
| CA | 1089874 | * | 11/1980 |
| JP | 50006234 | * | 3/1975 |
| JP | 10-140019 | | 5/1998 |
| JP | 10-147626 | | 6/1998 |
| JP | 10-158385 | | 6/1998 |

OTHER PUBLICATIONS

Berlin et al, Plasticheskie Mass, Sulfur-containing Oligoester Acrylates and Polymers Based on Them, 1971,1, pp. 15-18, w/English Abstract.*
Reactive & Functional Polymers: "A Novel Synthesis of Polyesters with Pendant Hydroxyl Groups by Polyaddition of Bis (oxetane) with Dicarboxylic Acids Catalyzed by Quaternary Onium Salts" Department of Applied Chemistry, Jan. 1997, pp. 19-25.
Chemistry Letters: New Addition Reactions of Cyclic Ethers with Esters and Thioesters Catalyzed by Quaternary Ammonium Salts or Crown Ether Complexes, Department of Applied Chemistry, 1991, pp. 697-700.
Abstract of Japanese Patent: Publication No.: 08-332613, dated Dec. 1996.
Abstract of Japanese Patent: Publication No.: 08-321393, dated Dec. 1996.

* cited by examiner

*Primary Examiner*—Paul A. Zucker
(74) *Attorney, Agent, or Firm*—Rader, Fishman & Grauer PLLC; Ronald P. Kananen

(57) ABSTRACT

An unsaturated monocarboxylic ester compound has at least two structures represented by the following general formula (1):

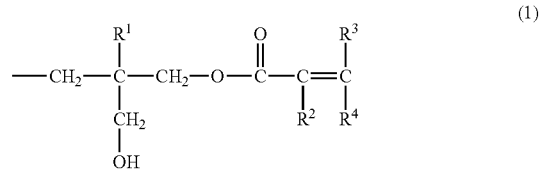

wherein $R^1$ represents a hydrogen atom or an alkyl group of 1 to 6 carbon atoms, and $R^2$, $R^3$ and $R^4$ independently represent a hydrogen atom, an alkyl group of 1 to 6 carbon atoms, an aryl group, an aralkyl group, a cyano group, a fluorine atom, or a furyl group. A curable composition comprises (A) the unsaturated carboxylic ester compound having two or more structures represented by the general formula (1) mentioned above, (B) a polymerization initiator, and optionally (C) a diluent.

2 Claims, 1 Drawing Sheet

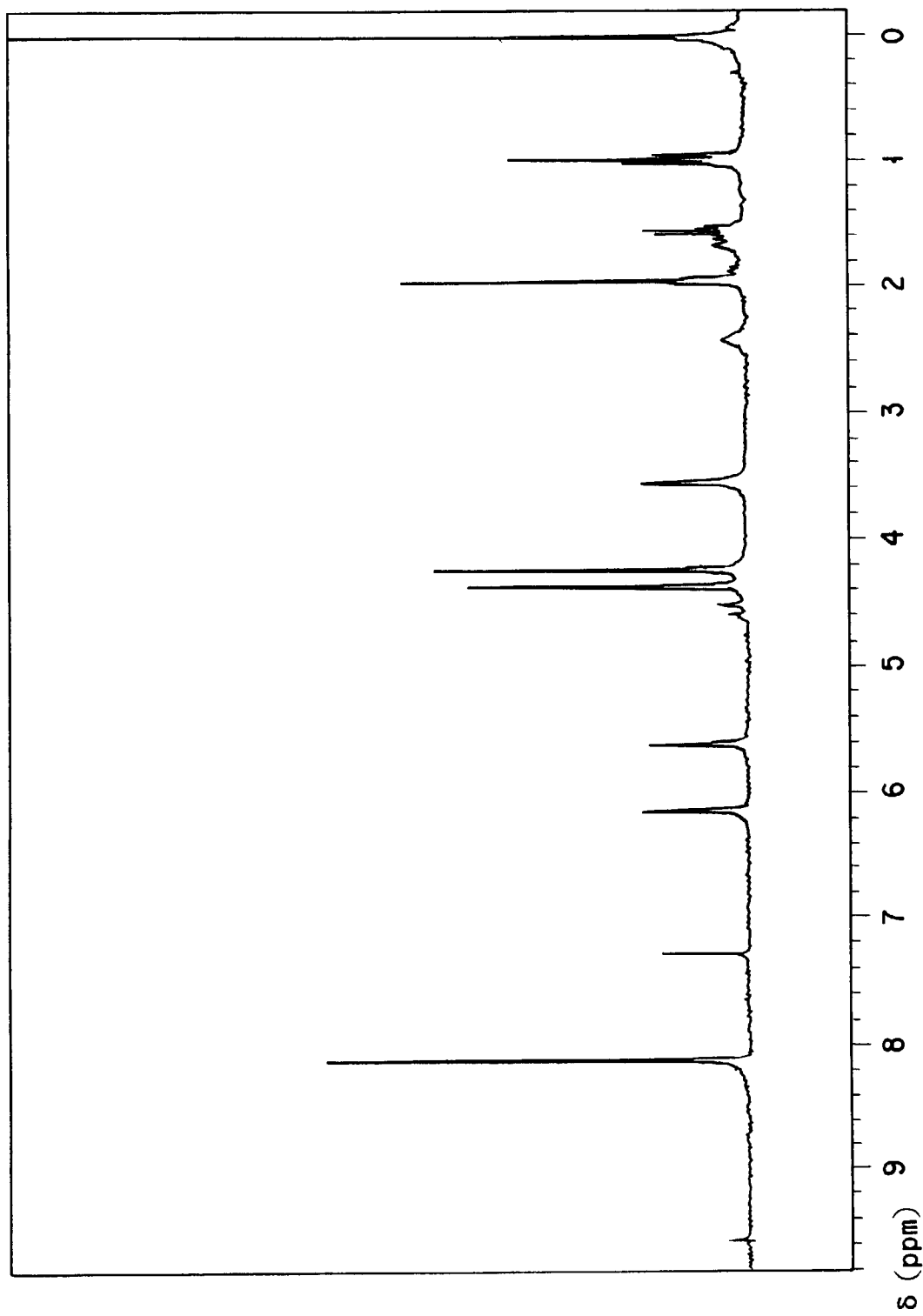

UNSATURATED CARBOXYLIC ESTER COMPOUND, PROCESS FOR PRODUCING THE SAME, AND COMPOSITION CURABLE WITH ACTINIC ENERGY RAY

CROSS-REFERENCE TO RELATED APPLICATIONS

This is a continuation of Application PCT/JP01/00447, filed Jan. 24, 2001, now abandoned.

BACKGROUND OF THE INVENTION

1. Field of the Invention

This invention relates to a new unsaturated carboxylic ester compound, particularly a polyfunctional unsaturated carboxylic ester compound, and a process for the production thereof. Since this unsaturated carboxylic ester compound has a photopolymerizable double bond, it can be advantageously used as a photocurable component and a reactive diluent, for example, of an actinic energy ray-curable composition which hardens by irradiation of an actinic energy ray.

The present invention further relates to a curable composition containing the above-mentioned unsaturated carboxylic ester compound, which composition hardens promptly by irradiation of an actinic energy ray such as an ultraviolet ray or an electron beam or further hardens by heating, thereby giving rise to a cured product excelling in adhesiveness to a substrate, particularly a composition curable with an actinic energy ray. This composition can be used in various application fields as adhesives, coating materials, and resist materials for printed circuit boards.

2. Description of the Prior Art

The curing of resin by irradiation of an actinic energy ray is widely utilized in painting of metal, coating of wood, printing ink, electronic materials, etc owing to its high curing speed and solvent-free. One of the materials mainly used in these fields is an epoxy acrylate. Since this compound is obtained by the reaction of an epoxy resin having an oxirane group which is a cyclic ether of three-membered ring and (meth)acrylic acid and contains a polymerizable unsaturated group, it is used in a photocurable composition by mixing with a compound which generates radicals by irradiation of an actinic energy ray (phtopolymerization initiator), and heretofore various studies thereof have been done. However, the composition containing this compound had the problem of being inferior in the adhesiveness to various substrates because the composition causes large shrinkage after photocuring and most of the hydroxyl groups caused by the modification reaction of an epoxy resin are secondary hydroxyl groups. For the purpose of solving such problems, the composition which employs the cationic polymerization of oxetane as a curing reaction has been proposed. However, the kinds of materials which can be used in this reaction are small in compared with a radically polymerizable monomer, it was possible to attain the desired properties of the cured product only with difficulty.

On the other hand, the organic reaction involving the addition reaction of an oxetane ring which is an ether of four-membered ring has been reported recently. For example, the addition reaction of an oxetane compound and an active ester (T. Nishikubo and K. Sato, Chem. Lett., 697 (1992)) and the synthesis of polyester having a primary hydroxyl group attached to a side chain thereof by the polyaddition reaction of a bisoxetane and a dicarboxylic acid (T. Nishikubo, A. Kameyama, and A. Suzuki, Reactive & Functional Polymers, 37, 19 (1998)) have been reported.

Furthermore, JP 10-168120,A discloses a method of producing a resin of the actinic energy ray-curing type by carrying out ring opening addition of an oxetane group-containing (meth)acrylate monomer to a carboxyl group-containing resin or by effecting ring opening addition of a carboxyl group-containing unsaturated monomer to an oxetane ring-containing resin. However, these articles make no mention of the compounds of the present invention and the actinic energy ray-curable compositions using them.

SUMMARY OF THE INVENTION

An object of the present invention is, therefore, to provide an unsaturated carboxylic ester compound which, when used as a photocurable component, cures promptly by short-time irradiation of an actinic energy ray or further by heating, thereby giving rise to a cured product excelling in adhesiveness to various substrates and many other properties, particularly a polyfunctional unsaturated carboxylic ester compound.

Another object of the present invention is to provide a process which is capable of producing such an unsaturated carboxylic ester compound with sufficient productivity.

A further object of the present invention is to provide a curable composition which hardens promptly by short-time irradiation of an actinic energy ray or further hardens by heating and allows a cured product excelling in adhesiveness and other properties to be obtained, particularly a composition curable with an actinic energy ray.

To accomplish the objects mentioned above, in accordance with one aspect of the present invention, there is provided an unsaturated carboxylic ester compound having at least two structures represented by the following general formula (1):

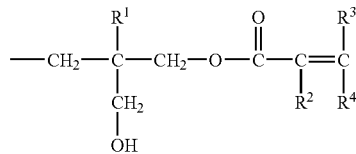

(1)

wherein $R^1$ represents a hydrogen atom or an alkyl group of 1 to 6 carbon atoms, and $R^2$, $R^3$ and $R^4$ independently represent a hydrogen atom, an alkyl group of 1 to 6 carbon atoms, an aryl group, an aralkyl group, a cyano group, a fluorine atom, or a furyl group.

The unsaturated carboxylic ester compound mentioned above is capable of curing promptly by irradiation of an actinic energy ray owing to the specific structure having a photopolymerizable unsaturated double bond and a primary hydroxyl group in combination. Furthermore, it is possible to thermally cure the compound by heat radicals owing to the presence of the unsaturated double bond and also by addition of a curing agent (for example, isocyanates) which can react with a hydroxyl group owing to the presence of the primary hydroxyl group at a side chain mentioned above. Particularly, in the case of a polyfunctional unsaturated carboxylic ester compound, it cures promptly by short-time irradiation of an actinic energy ray and the resultant cured product exhibits excellent adhesiveness to various substrates owing to the primary hydroxyl group.

In accordance with another aspect of the present invention, there is provided a process of producing an unsaturated carboxylic ester compound characterized by comprising causing the reaction of (a) a compound containing at least two oxetanyl groups with (b) an unsaturated carboxylic acid in the presence of a reaction promotor, thereby producing a compound having at least two structures represented by the general formula (1) mentioned above. According to such a process, the unsaturated carboxylic ester compound as mentioned above can be produced with a high yield.

According to yet another aspect of the present invention, there is provided a curable composition. One embodiment thereof contains (A) an unsaturated carboxylic ester compound having at least two structures represented by the general formula (1) mentioned above and (B) a polymerization initiator as indispensable components thereof. As a polymerization initiator to be used herein, a photopolymerization initiator (photo-radical polymerization initiator) and/ or a heat-radical polymerization initiator may be used.

Another preferred embodiment of the curable composition of the present invention contains (A) a polyfunctional unsaturated carboxylic ester compound having at least two structures represented by the general formula (1) mentioned, (B) a photopolymerization initiator, and (C) a diluent as indispensable components thereof.

In a preferred embodiment, the polyfunctional unsaturated carboxylic ester compound (A) mentioned above is a compound obtained by the addition reaction of (a) a polyfunctional oxetane compound containing at least two oxetanyl groups and (b) an unsaturated carboxylic acid and, as the above-mentioned unsaturated carboxylic acid (b), acrylic acid and/or methacrylic acid prove to be desirable.

The actinic energy ray-curable composition of the present invention containing the aforementioned polyfunctional unsaturated carboxylic ester compound as a photocurable component hardens by short-time irradiation of an actinic energy ray with little shrinkage on curing, and a cured product excelling in adhesiveness to various substrates and in dimensional stability is obtained.

BRIEF DESCRIPTION OF THE DRAWING

The single FIGURE shows the nuclear magnetic resonance spectrum of the unsaturated carboxylic ester compound obtained in Example 1.

DETAILED DESCRIPTION OF THE INVENTION

The present inventors, after pursuing a diligent study to solve the problems mentioned above, have found that an unsaturated carboxylic ester compound of the specific structure having a primary hydroxyl group produced by the ring opening reaction of an oxetane ring and a photopolymerizable unsaturated double bond is capable of curing promptly by irradiation of an actinic energy ray, that it is possible to thermally cure the compound by heat radicals owing to the presence of the unsaturated double bond and also by addition of a curing agent (for example, isocyanates) which can react with a hydroxyl group owing to the presence of the primary hydroxyl group at a side chain mentioned above, and further that the compound exhibits excellent adhesiveness to various substrates. The present inventors have further found that an actinic energy ray-curable composition containing the aforementioned compound as a photocurable component hardens by short-time irradiation of an actinic energy ray, thereby giving rise to a cured product excelling in adhesiveness to various substrates. Further, they have found an industrially advantageous process for producing such a compound. As a result, the present invention has been perfected.

Specifically, the unsaturated carboxylic ester compound having at least one structure represented by the general formula (1) mentioned above is capable of curing by irradiation of an actinic energy ray owing to the structure having a photopolymerizable unsaturated double bond, particularly (meth)acryloyl group. Particularly, in the case of a polyfunctional unsaturated carboxylic ester compound, it cures promptly by short-time irradiation of an actinic energy ray. Furthermore, it is possible to thermally cure the compound by heat radicals owing to the presence of the unsaturated double bond and also by addition of a curing agent (for example, isocyanates) which can react with a hydroxyl group owing to the presence of the primary hydroxyl group at a side chain mentioned above. The resultant cured product exhibits excellent adhesiveness to various substrates owing to the hydrogen bonding nature of the primary hydroxyl group.

The unsaturated carboxylic ester compound having a primary hydroxyl group and an unsaturated double bond in combination in its molecule represented by the general formula (1) mentioned above can be produced by causing the reaction of (a) a polyfunctional oxetane compound containing two or more oxetanyl groups with (b) an unsaturated carboxylic acid in the presence of a reaction promotor, such as a tertiary amine, a quaternary onium salt, and a tertiary phosphine. Incidentally, when a polyfunctional unsaturated carboxylic acid having two or more carboxyl groups is subjected to the addition reaction, a cross-linking reaction will take place, which will result in gelation. For that reason, the unsaturated carboxylic acid is used in the present invention. Since the resultant reaction product has a primary hydroxyl group, it is possible to obtain a cured product which has excellent adhesiveness to a substrate.

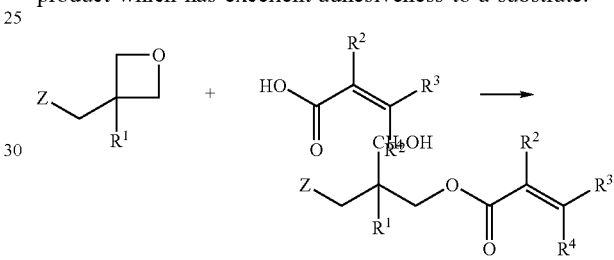

This reaction process is illustrated as follows.

The oxetane compound (a) to be used for the above-mentioned reaction is not limited to a particular one insofar as it has at least two oxetanyl groups in its molecule. In order to introduce two or more unsaturated double bonds and primary hydroxyl groups thereinto for the purpose of increasing the photocuring properties and adhesiveness, it is desirable to use a polyfunctional oxetane compound containing two or more oxetanyl groups in its molecule. Incidentally, in the case of the polyfunctional oxetane compound, it is preferred to have a branched from in terms of the printing properties or thixotropic properties of a composition containing the resultant product.

As typical examples of the compound containing two oxetane rings in its molecule, a bisoxetane represented by the following general formula (2) may be cited.

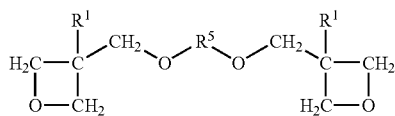

In the general formula (2) mentioned above, $R^1$ represents the same meaning as mentioned above, and $R^5$ represents a bivalent group selected from among linear or branched saturated hydrocarbons of 1 to 12 carbon atoms, linear or branched unsaturated hydrocarbons of 1 to 12 carbon atoms, aromatic hydrocarbons represented by the following formulas (A), (B), (C), (D), and (E), linear or cyclic alkylene groups containing a carbonyl group and represented by the following formulas (F) and (G), and aromatic hydrocarbons containing a carbonyl group and represented by the following formulas (H) and (I).

(A)

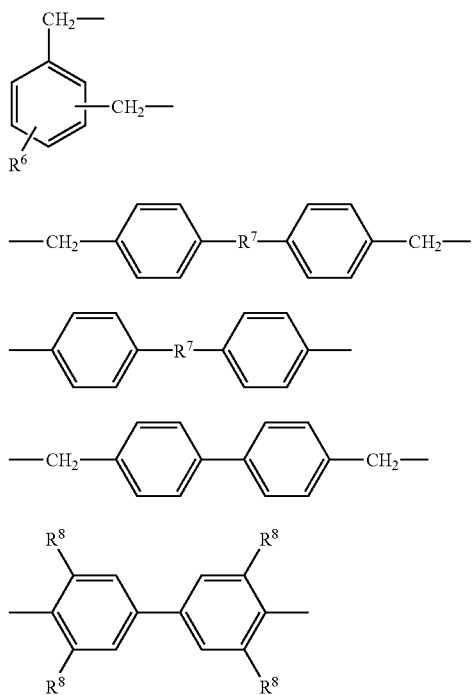

(B)

(C)

(D)

(E)

wherein $R^6$ represents a hydrogen atom, an alkyl group of 1 to 12 carbon atoms, an aryl group, or an aralkyl group, $R^7$ represents —O—, —S—, —CH$_2$—, —NH—, —SO$_2$—, —CH(CH$_3$)—, —C(CH$_3$)$_2$—, or —C(CF$_3$)$_2$—, and $R^8$ represents a hydrogen atom or an alkyl group of 1 to 6 carbon atoms.

(F)

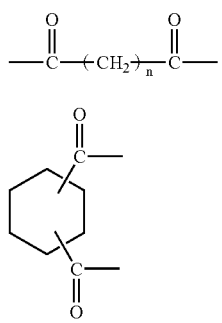

Wherein n represents an integer of 1 to 12.

(G)

(H)

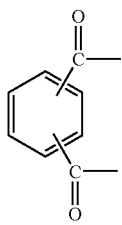

-continued (I)

As typical examples of the compound containing three or more oxetane rings in its molecule, etherified products of an oxetane with a hydroxyl group-containing resin such as a novolak resin, poly(p-hydroxy styrene), calixarene compounds, or a silicone resin like a silsesquioxane besides a compound represented by the following general formula (3) may be cited. In addition thereto, a copolymer of an unsaturated monomer containing an oxetane ring and an alkyl (meth)acrylate may be cited. The term "(meth)acrylate" as used in the present specification refers collectively to acrylate and methacrylate. This (3)

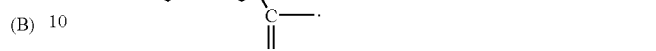

holds good for other similar expression.

In the general formula (3) mentioned above, $R^1$ represents the same meaning as mentioned above, and $R^9$ represents a residue of the hydroxyl group-containing resin of the etherified product mentioned above, a branched alkylene group of 1 to 12 carbon atoms represented by the following formula (J), (K) or (L), or an aromatic hydrocarbon represented by the following formula (M), (N) or (P), and m represents the number of functional groups bonded to the residue $R^9$, an integer of three or more, preferably an integer of 3 to 5,000.

(J)

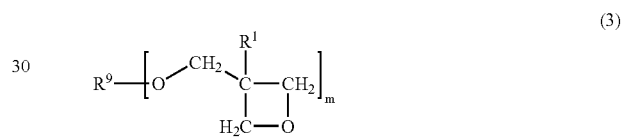

(K)

(L)

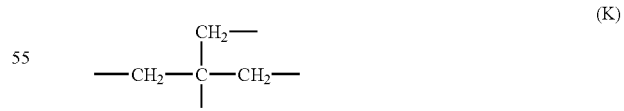

(M)

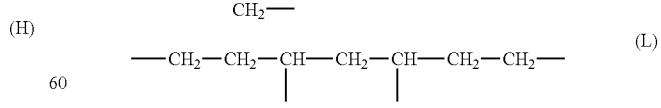

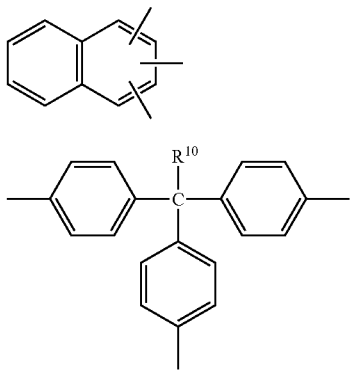

(N)

(P)

wherein $R^{10}$ represents a hydrogen atom, an alkyl group of 1 to 6 carbon atoms, or an aryl group.

As the unsaturated carboxylic acid (b) to be used for the reaction mentioned above, a compound containing a polymerizable unsaturated group and a carboxylic group in combination in its molecule is preferable. As concrete examples, acrylic acid, methacrylic acid, cinnamic acid, crotonic acid, sorbic acid, α-cyanocinnamic acid, β-styryl acrylic acid, etc. may be cited. Alternatively, a half ester of a dibasic acid anhydride with a (meth)acrylate having a hydroxyl group may be used. As concrete examples, the half esters of the acid anhydride such as phthalic acid, tetrahydrophthalic acid, hexahydrophthalic acid, maleic acid, and succinic acid with the hydroxyl group-containing (meth) acrylate such as hydroxyethyl acrylate, hydroxyethyl methacrylate, hydroxypropyl acrylate, and hydroxypropyl methacrylate may be cited. These unsaturated carboxylic acids may be used either singly or in the form of a combination of two or more members.

In the reaction mentioned above, the ratio of the oxetanyl group-containing compound (a) to the unsaturated carboxylic acid (b) (the charging ratio in the reaction mixture) is desired to be in the range of 0.1 to 3.0 mols, preferably 0.3 to 1.5 mols, more preferably 0.5 to 1.0 mol, of the unsaturated carboxylic acid per one mol of the oxetanyl group. If the proportion of the unsaturated carboxylic acid is lower than 0.1 mol per one mol of the oxetanyl group, the compound will be at a disadvantage in acquiring insufficient polymerizable groups introduced into the product and thus an unduly low photocuring properties. When the unsaturated carboxylic acid remains in the unreacted state, it may be removed by a well known method such as vacuum distillation and alkali cleaning.

When the unsaturated carboxylic ester compound of a higher molecular weight is needed, part of the unsaturated carboxylic acid (b) to be used for the reaction may be replaced with a polycarboxylic acid or polyphenol of bifunctionality or more functionality. Particularly, it is possible to obtain a linear macromolecular compound in the case of the bifunctional carboxylic acid or phenol and a branched macromolecular compound in the case of the trifunctional carboxylic acid or phenol. As concrete examples of the polycarboxylic acid, bifunctional carboxylic acids such as succinic acid, adipic acid, muconic acid, suberic acid, tetrahydrophtalic acid, hexahydrophtalic acid, hexahydroisophtalic acid, phtalic acid, isophtalic acid, and terephtalic acid, and trifunctional carboxylic acids such as 1,2,3-propane tricarboxylic acid, citric acid, aconitic acid, and trimellitic acid may be cited. As concrete examples of the polyphenol, bifunctional phenols such as catechol, resorcin, hydroquinone, 1,4-naphthalene diol, 1,5-naphthalene diol, bisphenol A, and biphenol, and trifunctional phenols such as 2,4,4'-trihydroxybenzophenone and 4,4',4"-methylidene trisphenol may be cited.

As a reaction promotor, any compound may be arbitrarily selected from among a tertiary amine, a tertiary amine salt, a quaternary onium salt, a tertiary phosphine, a crown ether complex, and a phosphonium ylide. These compounds may be used either singly or in the form of a combination of two or more members.

As the tertiary amine, triethylamine, tributylamine, DBU (1,8-diazabicyclo[5.4.0]undeca-7-ene), DBN (1,5-diazabicyclo[4.3.0]nona-5-ene), DABCO (1,4-diazabicyclo[2.2.2] octane), pyridine, N,N-dimethyl-4-amino pyridine, etc. may be cited.

As the tertiary amine salt, U-CAT series of Sun-Apro K.K., for example, may be cited.

As the quaternary onium salt, ammonium salts, phosphonium salts, arsonium salts, stibonium salts, oxonium salts, sulfonium salts, selenonium salts, stannonium salts, iodonium salts, etc. may be cited. Particularly preferable salts are ammonium salts and phosphonium salts. As concrete examples of the ammonium salts, tetra-n-butylammonium halide such as tetra-n-butylammonium chloride (TBAC), tetra-n-butylammonium bromide (TBAB), and tetra-n-butylammonium iodide (TBAI), and tetra-n-butylammonium acetate (TBAAc) may be cited. As concrete examples of the phosphonium salts, tetra-n-butylphosphonium halide such as tetra-n-butylphosphonium chloride (TBPC), tetra-n-butylphosphonium bromide (TBPB), and tetra-n-butylphosphonium iodide (TBBI), tetraphenylphosphonium halide such as tetraphenylphosphonium chloride (TPPC), tetraphenylphosphonium bromide (TPPB), and tetraphenylphosphonium iodide (TPPI), and ethyltriphenylphosphonium bromide (ETPPB), ethyltriphenylphosphonium acetate (ETPPAc), etc. may be cited.

As the tertiary phosphine, any trivalent organic phosphorus compounds containing an alkyl group of 1 to 12 carbon atoms or an aryl group may be used. As the concrete examples thereof, triethylphosphine, tributylphosphine, triphenylphosphine, etc. may be cited.

Further, a quaternary onium salt obtained by the addition reaction of the tertiary amine or the tertiary phosphine with a carboxylic acid or a highly acidic phenol may be used as the reaction promotor. They may be in the form of a quaternary salt before adding to the reaction system. Alternatively, they may be individually added to the reaction system so as to form the quaternary salt in the reaction system. As the concrete examples thereof, tributylamine acetic acid salt obtained from tributylamine and acetic acid and triphenylphosphine acetic acid salt formed from triphenylphosphine and acetic acid.

As concrete examples of the crown ether complex, complexes of crown ethers such as 12-crown-4,15-crown-5,18-crown-6, dibenzo-18-crown-6,21-crown-7, and 24-crown-8 with alkali metal salts such as lithium chloride, lithium bromide, lithium iodide, sodium chloride, sodium bromide, sodium iodide, potassium chloride, potassium bromide, and potassium iodide may be cited.

Although any known compounds obtained by the reaction of a phosphonium salt and a base may be used as the phosphonium ylide, a highly stable compound is preferable from the viewpoint of easy handling. As concrete examples thereof, (formylmethylene)triphenylphosphine, (acetylmethylene)triphenylphosphine, (pivaloylmethylene)triphenylphosphine, (benzoylmethylene)triphenylphosphine, (p-methoxybenzoylmethylene)triphenylphosphine, (p-methylbenzoylmethylene)triphenylphosphine, (p-nitrobenzoylmethylene)triphenylphosphine, (naphthoyl)triphenylphosphine, (methoxycarbonyl)triphenylphosphine, (diacetylmethylene)triphenylphosphine, (acetylcyano)triphenylphosphine, (dicyanomethylene)triphenylphosphine, etc. may be cited.

The amount of the reaction promotor to be used is preferred to be in the approximate range of 0.1 to 25 mol %, more preferably 0.5 to 20 mol %, most preferably 1 to 15 mol %, based on one mol of the oxetanyl group. If the amount of the reaction promotor to be used is less than 0.1 mol % of the oxetanyl group, the reaction will not proceed at a practical reaction speed. Conversely, a large amount exceeding 25 mol % is not desirable from the economical viewpoint because a remarkable reaction promotion effect will not be obtained even when the reaction promotor is present in such a large amount.

The reaction temperature is preferred to be in the approximate range of 100 to 200° C., more preferably 120 to 160° C. If the reaction temperature is lower than 100° C., the reaction will not proceed to a satisfactory extent. Conversely, the reaction temperature exceeding 200° C. is not desirable from the reasons that the reaction products will tend to cause the thermal polymerization due to the reaction of the double bonds thereof and that the unsaturated carboxylic acid having a low boiling point will evaporate. Although the reaction time may be suitably selected depending on the reactivity of the raw materials to be used and the reaction temperature, the preferred reaction time is about 5 to 72 hours.

Although the aforementioned reaction proceeds either in the presence of an organic solvent or in the absence of a solvent, the absence of the solvent is desirable from the viewpoint of the speed of the reaction. Alternatively, the reaction may be performed in the presence of a diluent because the presence of the diluent makes possible to suppress the increase in viscosity during the reaction. Although the diluent to be used is not limited to a particular one insofar as it can keep the reaction temperature, the diluents which can dissolve the raw material therein prove to be desirable. When the organic solvent is used as the diluent during the synthesis, the solvent may be removed by a well known method such as vacuum distillation. Furthermore, the production can be also carried out in the presence of a reactive monomer to be described hereinafter.

As the organic solvent, any known organic solvents may be used insofar as they will not exert a harmful influence on the reaction and can keep the reaction temperature. As concrete examples thereof, alcohols such as diethylene glycol monomethyl ether, diethylene glycol monoethyl ether, dipropylene glycol monomethyl ether, and dipropylene glycol monobutyl ether; glycol ethers such as ethylene glycol monomethyl ether acetate, diethylene glycol monomethyl ether acetate, diethylene glycol monoethyl ether acetate, propylene glycol monomethyl ether acetate, and dipropylene glycol monomethyl ether acetate; ethers such as diethylene glycol dimethyl ether and dipropylene glycol dimethyl ether; ketones such as methylisobutyl ketone and cyclohexanone; and aromatic hydrocarbons such as toluene and xylene may be cited.

By mixing a photo-radical polymerization initiator and/or a heat radical polymerization initiator which generate radicals by irradiation of an actinic energy ray or by heating as the polymerization initiator (B) with one or a mixture of two or more of the unsaturated carboxylic ester compounds, particularly the polyfunctional unsaturated carboxylic ester compounds (A) of the present invention obtained as described above, an actinic energy ray-curable composition or a thermosetting composition may be obtained. Further, by adding a reactive monomer as the diluent (C) to the composition, it is possible to improve the phtocuring properties thereof. Incidentally, the amount of the polyfunctional unsaturated carboxylic ester compounds (A) to be incorporated in the curable composition of the present invention, particularly the actinic energy ray-curable composition is not limited to a particular range.

As the photo-radical polymerization initiator to be used as the polymerization initiator (B), any known compounds which generate radicals by irradiation of an actinic energy ray may be used. As concrete examples thereof, benzoin and alkyl ethers thereof such as benzoin, benzoin methyl ether, and benzoin ethyl ether; acetophenones such as acetophenone, 2,2-dimethoxy-2-phenyl acetophenone and 4-(1-t-butyldioxy-1-methylethyl) acetophenone; anthraquinones such as 2-methylanthraquinone, 2-amylanthraquinone, 2-t-butyl anthraquinone, and 1-chloroanthraquinone; thioxanthones such as 2,4-dimethylthioxanthone, 2,4-diisopropylthioxanthone, and 2-chlorothioxanthone; ketals such as acetophenone dimethyl ketal and benzyl dimethyl ketal; benzophenones such as benzophenone, 4-(1-t-butyldioxy-1-methylethyl) benzophenone, and 3,3',4,4'-tetrakis(t-butyldioxycarbonyl) benzophenone; aminoacetophenones such as 2-methylthio-1-[4-(methylthio)phenyl]-2-morpholino-propane-1-one and 2-benzyl-2-dimethylamino-1-(4-morpholinophenyl)-butane-1-one; alkylphosphines such as 2,4,6-trimethylbenzoyl phosphine oxide; and acryzines such as 9-phenyl acryzine may be cited.

These well known and widely used photo-radical polymerization initiators may be used either singly or in the form of a combination of two or more members. The amount of the photo-radical polymerization initiator to be used is preferred to be in the range of from 0.1 to 30 parts by weight, based on 100 parts by weight of the unsaturated carboxylic ester compound (A) mentioned above. If the amount of the photo-radical polymerization initiator to be used is less than the lower limit of the range mentioned above, the composition will not be photocured by irradiation of an actinic energy ray or the irradiation time should be prolonged, and a coating film of satisfactory properties will be obtained only with difficulty. Conversely, even if the photo-radical polymerization initiator is added to the composition in a large amount exceeding the upper limit of the range mentioned above, the composition will not attain the further improvement in the curing properties and such a large amount is not desirable from the economical viewpoint.

In the curable composition of the present invention, for the purpose of improving the curing with an actinic energy ray, a curing promotor and/or sensitizer may be used in combination with the photo-radical polymerization initiator mentioned above. As the curing promoters which are usable herein, tertiary amines such as triethylamine, triethanolamine, 2-dimethylaminoethanol, N,N-(dimethylamino)ethyl benzoate, N,N-(dimethylamino)isoamyl benzoate, and pentyl-4-dimethylamino benzoate; and thioethers such as β-thioglycol may be cited. As the sensitizer, sensitizing dyestuff such as (keto)cumalin and thioxantene; and alkyl borates of such dyestuff as cyanine, rhodamine, safranine, malachite green, and methylene blue may be cited. These curing promotors and/or sensitizers may be used independently either singly or in the form of a combination of two or more members. The amount of the curing promotors and/or sensitizers to be used is preferred to be in the range of from 0.1 to 30 parts by weight, based on 100 parts by weight of the unsaturated carboxylic ester compound mentioned above.

As the heat radical polymerization initiators which are usable in the present invention, organic peroxides such as benzoyl peroxide, acetyl peroxide, methyl ethyl ketone peroxide, lauroyl peroxide, dicumyl peroxide, di-t-butyl peroxide, t-butyl hydroperoxide, and cumene hydroperoxide; azo type initiators such as 2,2'-azobisisobutyronitrile, 2,2'-azobis-2-methylbutyronitrile, 2,2'-azobis-2,4-divaleronitrile, 1,1'-azobis(1-acetoxy-1-phenylethane), 1'-azobis-1-cyclohexane carbonitrile, dimethyl-2,2'-azobisisobutylate, 4,4'-azobis-4-cyanovalic acid, and 2-methyl-2,2'-azobispropanenitrile may be cited. As the preferred initiator, 1,1'-azobis(1-acetoxy-1-phenylethane) is cited because it is the non-cyane and non-halogen type. The heat radical polymerization initiator is used in the range of from 0.1 to 10 parts by weight, preferably from 0.5 to 5 parts by weight, based on 100 parts by weight of the unsaturated carboxylic ester compound mentioned above.

When an organic peroxide which exhibits a lower curing rate is used as the heat radical polymerization initiator, tertiary amines such as tributylamine, triethylamine, dimethyl-p-toluidine, dimethylaniline, triethanolamine, and diethanolamine, or metallic soap such as cobalt naphthenate, cobalt octoate, and manganous naphthenate may be used as a promotor.

Further, when the addition reaction of the oxetane compound and the unsaturated carboxylic acid is carried out in such a proportion that the equivalent weight ratio of the unsaturated carboxylic acid to the oxetanyl group is less than 1.0 mol (i.e., the case that the oxetane ring remains in the resultant ester compound), it is possible to make the actinic energy ray-curable composition of the present invention to form the radical-cationic hybrid curing system by mixing into the composition a cationic polymerization initiator which initiates the cationic polymerization by irradiation of an actinic energy ray. Thus, it is possible to obtain a cured product by using the cationic polymerization in combination. As the cationic polymerization initiator, various known cationic polymerization initiators such as diaryl iodonium salts, triaryl sulfonium salts, thiobistriaryl sulfonium salts, selenonium salts, phosphonium salts may be used. These cationic polymerization initiators may be used either singly or in the form of a mixture of two or more members. The amount of the cationic polymerization initiator to be incorporated in the actinic energy ray-curable composition may be in the conventionally used range, in general not less than 0.05 part by weight, preferably not less than 0.1 part by weight, most preferably in the range of 0.5 to 10 parts by weight, based on 100 parts by weight of the unsaturated carboxylic ester compound.

The actinic energy ray-curable composition of the present invention may incorporate a diluent (C) therein at the time of the synthesis or after the synthesis. As the diluent (C), a compound having a polymerizable group which is capable of taking part in the curing rection can be advantageously used. Any known reactive diluents such as monofunctional acrylates and/or polyfunctional acrylates can be used. As concrete examples thereof, methyl (meth)acrylate, ethyl (meth)acrylate, n-butyl (meth)acrylate, isobutyl (metha)crylate, 2-ethylhexyl (meth)acrylate, isodecyl (meth)acrylate, lauryl (meth)acrylate, tridecyl (meth)acrylate, stearyl (meth)acrylate, methoxypolyethylene glycol (meth)acrylate, cyclohexyl (meth)acrylate, tetrahydrofurfuryl (meth)acrylate, isobornyl (meth)acrylate, benzyl (meth)acrylate, 2-hydroxyethyl (meth)acrylate, 2-hydroxypropyl (meth)acrylate, 2-hydroxybutyl (meth)acrylate, dimethylaminoethyl (meth)acrylate, ethylene glycol di(meth)acrylate, diethylene qlycol di(meth)acrylate, 1,4-butanediol di(meth)acrylate, 1,6-hexanediol di(meth)acrylate, trimethylol propane tri(meth)acrylate, glycerin di(meth)acrylate, pentaerythritol tri(meth)acrylate, pentaerythritol tetra(meth)acrylate, dipentaerythritol hexa(meth)acrylate, polyester acrylate, reaction products of dibasic acid anhydrides with alcohols having one or more unsaturated groups in its molecule, etc. may be cited. Further, it is possible to add the organic solvent as mentioned above to the composition as the diluent for the purpose of adjusting the viscosity of the composition. The diluents (c) can be used either singly or in the form of a mixture of two or more members and the amount thereof is not limited to a particular range.

In order to obtain a cured product in the radical-cationic hybrid curing system, a monofunctional and/or polyfunctional oxetane compound my be added to the composition besides the diluent (C) mentioned above. As concrete examples thereof, monofunctional oxetanes such as 3-methyl-3-hydroxymethyloxetane, 3-ethyl-3-hydroxymethyloxetane, 3-methyl-3-hexyloxymethyloxetane, 3-ethyl-3-hexyloxymethyloxetane, 3-methyl-3-(2-ethylhexyloxymethyl)oxetane, 3-ethyl-3-(2-ethylhexyloxymethyl)oxetane, 3-methyl-3-benzyloxymethyloxetane, 3-ethyl-3-benzyloxymethyloxetane, 3-methyl-3-phenoxymethyloxetane, and 3-ethyl-3-phenoxymethyloxetane; and polyfunctional oxetanes such as oligomers or copolymers of bis[(3-methyl-3-oxetanylmethoxy)methyl]ether, bis[(3-ethyl-3-oxetanylmethoxy)methyl]ether, 1,4-bis[(3-methyl-3-oxetanylmethoxy)methyl]benzene, 1,4-bis[(3-ethyl-3-oxetanylmethoxy)methyl]benzene, (3-methyl-3-oxetanyl)methyl acrylate, (3-ethyl-3-oxetanyl)methyl acrylate, (3-methyl-3-oxetanyl)methyl methacrylate, and (3-ethyl-3-oxetanyl)methyl methacrylate may be cited.

The actinic energy ray-curable composition of the present invention may incorporate therein a polymer containing at least one epoxy group and/or vinyl ether group in its molecule or further an oxetane ring-containing compound or polymer in an amount such that the photocuring properties of the composition are not impaired. For example, for the purpose of improving the properties of a cured product, epoxy resins and such resins as a polyether resin, a polyester resin, an alkyd resin, a urethane resin and a silicone resin independently having an epoxy group or a vinyl ether group may be mixed into the composition. As the epoxy resins, a bisphenol A type epoxy resin, a bisphenol F type epoxy resin, a bisphenol S type epoxy resin, a phenol novolak type epoxy resin, a cresol novolak type epoxy resin, a glycidyl type epoxy resin, a cycloaliphatic type epoxy resin, etc. may be cited. As the oxetane ring-containing resins, a bisphenol A type oxetane resin, a biphenyl type oxetane resin, a phenol novolak type oxetane resin, a cresol novolak type oxetane resin, a copolymer of oxetane (meth)acrylate and alkyl (meth)acrylate, etc. may be cited. Further, for the sake of promoting the reaction of these resins, the composition may incorporate therein a small amount of a known epoxy curing promotor such as amine compounds, imidazole compounds, carboxylic acids, phenols, quaternary ammonium salts, and methylol group-containing compounds. By the addition of these thermosetting components to the composition, it is also possible to thermally cure the composition by heating the resultant coating film and to improve various properties such as hardness, resistance to chemicals, and heat resistance.

Further, the actinic energy ray-curable composition mentioned above may incorporate therein a compound containing at least one epoxy group and/or vinyl ether group in its molecule such as 3,4-epoxycyclohexyl vinyl ether, ethylene glycol monoglycidyl monovinyl ether, triethylene glycol monoglycidyl monovinyl ether, dipropylene glycol monoglycidyl monovinyl ether, cyclohexyl vinyl ether, benzyl vinyl ether, 2-ethylhexyl vinyl ether, triethylene glycol divinyl ether, dipropylene glycol divinyl ether, 1,4-bisdivinyloxymethyl cyclohexane, an adduct of isophorone diisocyanate with 4-hydroxybutyl vinyl ether in 1:2 molar ratio, and an adduct of hydogenated xylylene diisocyanate with 4-hydroxybutyl vinyl ether in 1:2 molar ratio.

Moreover, the actinic energy ray-curable composition of the present invention may incorporate therein, as occasion demands, a well known and widely used filler such as barium sulfate, silica, talc, clay, and calcium carbonate, a well known and widely used coloring pigment such as phthalocyanine blue, phthalocyanine green, titanium oxide, and carbon black, and other various additives such as an anti-foaming agent, an adhesiveness-imparting agent, a leveling agent, and a thermal polymerization inhibitor.

As the light sources for the irradiation of the actinic energy ray which are advantageously used for the purpose of curing the actinic energy ray-curable composition mentioned above include a low-pressure mercury lamp, a medium-pressure mercury lamp, a high-pressure mercury lamp, an ultra-high-pressure mercury lamp, a xenon lamp, and a metal halide lamp, for example. Laser beams can be utilized as the actinic ray for exposure. Further, electron beams, α-rays, β-rays, γ-rays, X-rays, neutron beams, etc. may be utilized.

Now, the present invention will be described more specifically below with reference to working examples and comparative examples, but the present invention is not limited to such examples. Wherever the term "parts" is used hereinbelow, it shall refer to "parts by weight" unless otherwise specified.

Examples of Synthesis of Unsaturated Carboxylic Ester Compounds

EXAMPLE 1

In a 30 ml flask made of glass, 3.62 g (10 millimols) of terephthalate bisoxetane, 3.44 g (40.0 millimols) of methacrylic acid, 0.42 g (1.0 millimol) of tetraphenylphosphonium bromide, 0.01 g of methoquinone, and 5 ml of xylene were charged and stirred with a magnet stirrer to left reacting for 24 hours at 130° C. After completion of the reaction, 50 ml of toluene and 40 ml of a 10% sodium carbonate aqueous solution were added to the mixture, the organic layer was removed by using a separatory funnel, and the organic layer was washed with water twice. After anhydrous sodium sulfate was added to the obtained organic layer, it was dried. Then, after the organic solvent was removed by distillation under vacuum, 5.6 g of thin brown viscous liquid was obtained. As a result of the HPLC analysis, it has been confirmed that the degree of conversion was 93%. By the measurement of IR spectrum of the product, the decrease in absorption caused by the oxetanyl group at 980 cm$^{-1}$ was confirmed. Further, in the $^1$H-NMR measurement the signal based on the oxetanyl group at 4.55 ppm disappeared and signals originated from the addition product at 3.5 ppm, 4.2 ppm and 4.4 ppm appeared as new signals. Therefore, the compound obtained was identified as the bifunctional methacrylic ester represented by the following formula (4). The nuclear magnetic resonance spectrum (solvent: CDCl$_3$, reference substance: TMS (tetramethyl silane)) of the compound obtained is shown in the FIGURE.

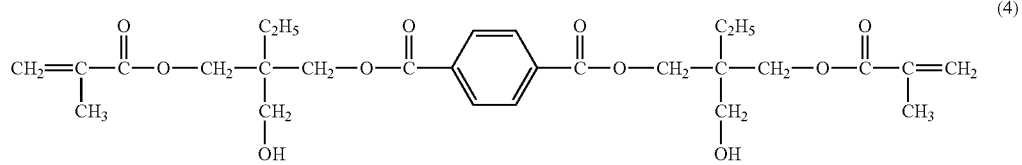

(4)

EXAMPLE 2

The synthesis was carried out by following the procedure of Example 1 mentioned above, except that 2.84 g (40.0 millimols) of acrylic acid was used in place of methacrylic acid. As a result of the reaction, 4.7 g of brown viscous liquid was obtained and the degree of conversion was 91%. In the measurement of IR spectrum of the product, the decrease in absorption caused by the oxetanyl group at 980 cm$^{-1}$ was found. Therefore, it has been confirmed that the addition reaction proceeded properly and the compound aimed at was produced.

EXAMPLE 3

In a 200 ml flask made of glass, 36.2 g (0.1 mol) of terephthalate bisoxetane, 17.2 g (0.2 mol) of methacrylic acid, 2.64 g (5.0 millimols) of tetraphenylphosphonium bromide, and 0.2 g of methoquinone were charged and stirred for 24 hours at 130° C. without using a solvent. The reaction product exhibited an acid value of 23.7 mg KOH/g and the rate of addition reaction was 85%. The hydroxyl value of the product was 141 mg KOH/g.

EXAMPLE 4

In a 200 ml flask made of glass, 36.2 g (0.1 mol) of terephthalate bisoxetane, 17.2 g (0.2 mol) of methacrylic acid, 2.64 g (5.0 millimols) of tetraphenylphosphonium bromide, and 0.2 g of methoquinone were charged and stirred for 12 hours at 150° C. At this time, the reaction mixture had an acid value of 0 mg KOH/g. The hydroxyl value of the reaction product was 150 mg KOH/g.

EXAMPLE 5

In a 200 ml flask made of glass, 36.2 g (0.1 mol) of xylylene bisoxetane, 17.2 g (0.2 mol) of methacrylic acid, 2.64 g (0.01 mol) of triphenylphosphine, and 0.2 g of methoquinone were charged and stirred for 36 hours at 130° C. At this time, the reaction mixture had an acid value of 0 mg KOH/g. The hydroxyl value of the reaction product was 207 mg KOH/g.

EXAMPLE 6

In a 200 ml flask made of glass, 36.2 g (0.1 mol) of terephthalate bisoxetane, 17.2 g (0.2 mol) of methacrylic acid, 2.1 g (0.005 mol) of tetraphenylphosphonium bromide, and 0.2 g of methoquinone were charged and stirred for 15 hours at 130° C. The reaction product exhibited an acid value of 23.7 mg KOH/g. The varnish thus obtained will be referred to hereinafter as "A varnish".

EXAMPLE 7

In a 200 ml flask made of glass, 36.2 g (0.1 mol) of terephthalate bisoxetane, 17.2 g (0.2 mol) of methacrylic acid, 2.64 g (0.01 mol) of triphenylphosphine, and 0.2 g of methoquinone were charged and stirred for 24 hours at 130° C. The reaction product exhibited an acid value of 23.7 mg KOH/g. The varnish thus obtained will be referred to hereinafter as "B varnish".

EXAMPLE 8

In a 200 ml flask made of glass, 36.2 g (0.1 mol) of xylylene bisoxetane, 17.2 g (0.2 mol) of methacrylic acid, 2.1 g (0.005 mol) of tetraphenylphosphonium bromide, and 0.2 g of methoquinone were charged and stirred for 24 hours at 140° C. The reaction product exhibited an acid value of 13.5 mg KOH/g. The varnish thus obtained will be referred to hereinafter as "C varnish".

EXAMPLE 9

The synthesis was carried out by following the procedure of Example 6, except that the amount of methacrylic acid was changed to 8.6 g (0.1 mol). As a result, a compound having an oxetane ring and an unsaturated double bond in combination was obtained. The varnish thus obtained will be referred to hereinafter as "D varnish".

Examples of Actinic Energy Ray-Curable Composition

EXAMPLE 10

The following components using the A varnish obtained in Example 6 were kneaded with a three-roll mill to obtain an actinic energy ray-curable composition.

| | |
|---|---|
| A varnish | 100 parts |
| Pentaerythritol triacrylate | 10 parts |
| Irgacure 184 (photopolymerization initiator manufactured by Ciba Specialty Chemicals Co.) | 3 parts |
| Silicone type anti-foaming agent | 1 part |
| Hydroxyethyl methacrylate | 5 parts |
| Total | 119 parts |

This composition was applied to a copper plate by using a bar coater in a thickness of 25 μm and irradiated with an actinic energy ray by the use of an ultraviolet light conveyor exposure device (light source: metal halide lamp) till a calculated dose of 3,000 mJ/cm². As a result, the composition was completely cured and a rigid film which does not dissolve in tetrahydrofuran (TFH) was formed.

EXAMPLE 11

The following components using the B varnish obtained in Example 7 were kneaded with a three-roll mill to obtain an actinic energy ray-curable composition.

| | |
|---|---|
| B varnish | 100 parts |
| Pentaerythritol triacrylate | 10 parts |
| Irgacure 184 | 3 parts |
| Silicone type anti-foaming agent | 1 part |
| Hydroxyethyl methacrylate | 5 parts |
| Total | 119 parts |

This composition was applied to a copper plate and irradiated with an actinic energy ray in the similar manner as in Example 10. As a result, the composition was completely cured and a rigid film was formed.

EXAMPLE 12

The following components using the C varnish obtained in Example 8 were kneaded with a three-roll mill to obtain an actinic energy ray-curable composition.

| | |
|---|---|
| C varnish | 100 parts |
| Pentaerythritol triacrylate | 10 parts |
| Irgacure 184 | 3 parts |
| Silicone type anti-foaming agent | 1 part |
| Hydroxyethyl methacrylate | 5 parts |
| Total | 119 parts |

This composition was applied to a copper plate and irradiated with an actinic energy ray in the similar manner as in Example 10. As a result, the composition was completely cured and a rigid film was formed.

EXAMPLE 13

The following components using the D varnish obtained in Example 9 were kneaded with a three-roll mill to obtain an actinic energy ray-curable composition.

| | |
|---|---|
| D varnish | 100 parts |
| Dipentaerythritol hexaacrylate | 10 parts |
| Irgacure 184 | 3 parts |
| SP-150 (cationic polymerization initiator manufactured by Asahi Denka Kogyo K.K.) | 3 parts |
| 3-ethyl-3-hydroxymethyl oxetane | 10 parts |
| Total | 126 parts |

This composition was applied to a copper plate and irradiated with an actinic energy ray in the similar manner as in Example 10. As a result, a tack-free coating film was formed.

COMPARATIVE EXAMPLE 1

The following components were kneaded with a three-roll mill to obtain an actinic energy ray-curable composition.

| | |
|---|---|
| Epoxy acrylate (Acrylated product of EPIKOTE 1001 (product of Yuka-Shell Epoxy K.K.)) | 100 parts |
| Pentaerythritol triacrylate | 10 parts |
| Irgacure 184 | 3 parts |
| Silicone type anti-foaming agent | 1 part |
| Hydroxyethyl methacrylate | 10 parts |
| Total | 124 parts |

This composition was applied to a copper plate and irradiated with an actinic energy ray in the similar manner as in Example 10. As a result, a tack-free coating film was formed. However, it has been found that cracks occurred in the coating film due to volume shrinkage on curing and the separation thereof from the base material was observed.

Since the aforementioned unsaturated carboxylic ester compound of the present invention has a photopolymerizable unsaturated double bond and a primary hydroxyl group in combination, it is capable of curing promptly by irradiation of an actinic energy ray, thermally curing by heat radicals owing to the presence of the unsaturated double bond and also thermally curing by addition of a curing agent (for example, isocyanates) which can react with a hydroxyl group owing to the presence of the primary hydroxyl group at a side chain mentioned above. Accordingly, this compound can be used as a curable component in various application fields. Particularly, in the case of a polyfunctional unsaturated carboxylic ester compound, it cures promptly by short-time irradiation of an actinic energy ray and the resultant cured product exhibits excellent adhesiveness to various substrates owing to the primary hydroxyl group. Accordingly, the polyfunctional unsaturated carboxylic ester compound of the present invention can be advantageously used in various application fields as a photocurable component and a reactive diluent, for example, of an actinic energy ray-curable composition which hardens by irradiation of an actinic energy ray.

Further, the curable composition of the present invention containing such an unsaturated carboxylic ester compound as a curable component, particularly the actinic energy ray-curable composition containing the polyfunctional unsaturated carboxylic ester compound as a photocurable component makes possible to obtain a cured product excelling in dimensional stability with little shrinkage on curing by short-time irradiation of an actinic energy ray. Accordingly, this composition can be advantageously used in various application fields as various kinds of protective film, coating materials, adhesives, sealing compounds, printing ink, electrical insulating materials, various resists and interlaminar insulating materials for printed circuit boards, and the like.

While certain specific working examples have been disclosed herein, the invention may be embodied in other specific forms without departing from the spirit or essential characteristics thereof. The described examples are therefore to be considered in all respects as illustrative and not restrictive, the scope of the invention being indicated by the appended claims rather than by the foregoing description and all changes which come within the meaning and range of equivalency of the claims are, therefore, intended to be embraced therein.

What is claimed is:

1. An unsaturated carboxylic ester compound derived from the reaction of (a) an oxetane compound containing at least two oxetanyl groups with (b) an unsaturated monocarboxylic acid and having at least two discrete structures represented by the following general formula (1):

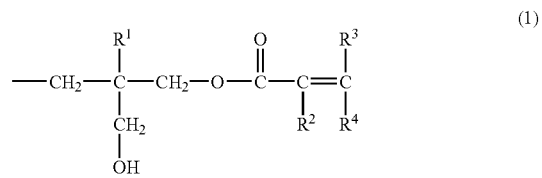

wherein $R^1$ represents a hydrogen atom or an alkyl group of 2 to 6 carbon atoms, $R^2$ represents a hydrogen atom or a methyl group, and $R^3$ and $R^4$ independently represent a hydrogen atom, wherein said oxetane compound (a) is selected from the group consisting of a bisoxetane compound represented by the following general formula (2) and a polyfunctional oxetane compound represented by the following general formula (3), and said unsaturated monocarboxylic acid (b) is selected from the group consisting of acrylic acid and methacrylic acid,

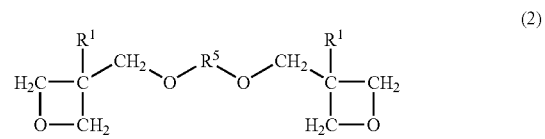

wherein, $R^1$ represents a hydrogen atom or an alkyl group of 2 to 6 carbon atoms, and $R^5$ represents a bivalent group selected from the group consisting of linear or branched saturated hydrocarbons of 2 to 12 carbon atoms, linear or branched unsaturated hydrocarbons of 2 to 12 carbon atoms, aromatic hydrocarbons represented by the following formulas (A), (B), (C), (D), and (E):

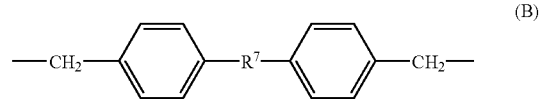

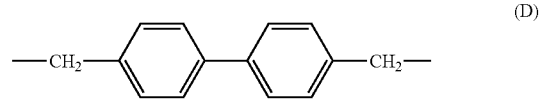

-continued

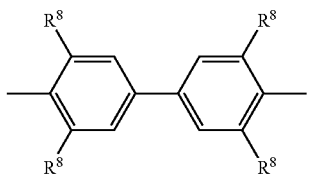
(E)

wherein $R^6$ represents a hydrogen atom, an alkyl group of 1 to 12 carbon atoms, an aryl group, or an aralkyl group, $R^7$ represents —O—, —S—, —CH$_2$—, —NH—, —SO$_2$—, —CH(CH$_3$)—, —C(CH$_3$)$_2$—, or —C(CF$_3$)$_2$—, and $R^8$ represents a hydrogen atom or an alkyl group of 1 to 6 carbon atoms, linear or cyclic alkylene groups containing a carbonyl group and represented by the following formulas (F) and (G):

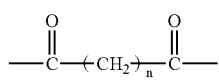
(F)

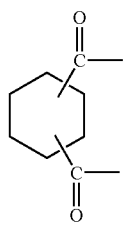
(G)

wherein n represents an integer of 1 to 12, and aromatic hydrocarbons containing a carbonyl group and represented by the following formulas (H) and (I):

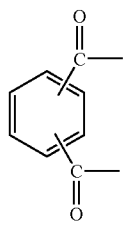
(H)

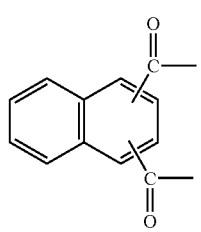
(I)

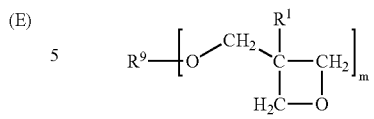
(3)

wherein, m represents the number of functional groups bonded to a residue $R^9$ and an integer of not less than three, $R^1$ represents a hydrogen atom or an alkyl group of 2 to 6 carbon atoms, and $R^9$ represents a residue of an etherified product with oxetane and either one of a novolak resin residue, a poly(p-hydroxy styrene) residue, a calixarene residue, a residue of a silicone resin, a branched alkylene group represented by the following formula (J), (K) or (L):

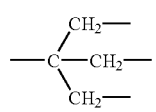
(J)

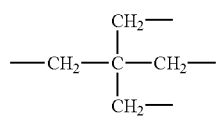
(K)

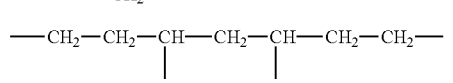
(L)

or an aromatic hydrocarbon represented by the following formula (M), (N) or (P):

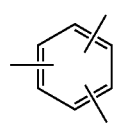
(M)

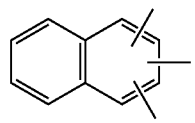
(N)

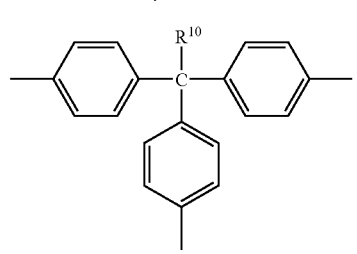
(P)

wherein $R^{10}$ represents a hydrogen atom, an alkyl group of 1 to 6 carbon atoms, or an aryl group.

2. The unsaturated carboxylic ester compound according to claim 1, wherein the substituent $R^1$ in said general formula (1) is an ethyl group.

* * * * *

UNITED STATES PATENT AND TRADEMARK OFFICE
CERTIFICATE OF CORRECTION

PATENT NO. : 7,057,063 B2
APPLICATION NO. : 10/370379
DATED : February 19, 2003
INVENTOR(S) : Robert Carson et al.

It is certified that error appears in the above-identified patent and that said Letters Patent is hereby corrected as shown below:

On Title Page, col. 1 Item (75)

Please correct the "Inventors" section to read as follows:

Robert Carson, Rahway, NJ (US); Susanne Teklits Iobst, Maywood, NJ (US); Salvatore E. San Philip, Belleville, NJ (US); Christina H. Arce, Cliffside Park, NJ (US); Carol Feinberg, Wayne, NJ (US)

Signed and Sealed this

Seventh Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,057,063 B2  
APPLICATION NO. : 10/202092  
DATED : June 6, 2006  
INVENTOR(S) : Tadatomi Nishikubo Page 1 of 1

It is certified that error appears in the above-identified patent and that said Letters Patent is hereby corrected as shown below:

Column 20:  
Line 17, "10" should be deleted.

Signed and Sealed this

Twenty-first Day of November, 2006

JON W. DUDAS  
*Director of the United States Patent and Trademark Office*

UNITED STATES PATENT AND TRADEMARK OFFICE
CERTIFICATE OF CORRECTION

PATENT NO. : 7,057,063 B2
APPLICATION NO. : 10/202092
DATED : June 6, 2006
INVENTOR(S) : Tadatomi Nishikubo et al.

Page 1 of 1

It is certified that error appears in the above-identified patent and that said Letters Patent is hereby corrected as shown below:

This certificate supersedes Certificate of Correction issued November 7, 2006, should be vacated since no Certificate of Correction was granted for this patent number.

Signed and Sealed this

Twelfth Day of December, 2006

JON W. DUDAS
*Director of the United States Patent and Trademark Office*